(12) United States Patent
Jackson (10) Patent No.: US 9,044,495 B2
(45) Date of Patent: Jun. 2, 2015

(54) NUCLEIC ACID LIGANDS TO LL37

(75) Inventor: George W. Jackson, Pearland, TX (US)

(73) Assignee: Biotex, Inc., Houston, TX (US)

( * ) Notice: Subject to any disclaimer, the term of this patent is extended or adjusted under 35 U.S.C. 154(b) by 0 days.

(21) Appl. No.: 13/296,163

(22) Filed: Nov. 14, 2011

(65) Prior Publication Data
US 2012/0121533 A1 May 17, 2012

Related U.S. Application Data (60) Provisional application No. 61/412,929, filed on Nov. 12, 2010.

(51) Int. Cl.
A61K 31/80 (2006.01)
A61P 17/00 (2006.01)
C07H 21/04 (2006.01)
A61K 31/713 (2006.01)

(52) U.S. Cl.
CPC .................................. A61K 31/713 (2013.01)

(58) Field of Classification Search
CPC ....... A61K 31/713; C07H 21/04; C07H 15/00
USPC ...................... 514/44 R, 46, 47, 50, 51, 18.6; 424/78.36
See application file for complete search history.

(56) References Cited

U.S. PATENT DOCUMENTS

2006/0275303 A1* 12/2006 Bals et al. .................. 424/155.1
2012/0295862 A1* 11/2012 Hrdlicka et al. ................ 514/46

* cited by examiner

Primary Examiner — Janet Epps-Smith
(74) Attorney, Agent, or Firm — Christopher Quan (57) ABSTRACT The present invention is directed to nucleic acid ligands to LL37, methods for producing said nucleic acid ligands, and methods for utilizing said nucleic acid ligands. In one exemplary embodiment, for example, this invention relates to nucleic acid ligands exhibiting high specific binding affinity to LL37 peptides, precursors and/or portions thereof. Further, the nucleic acid ligands may bind competitively with native ligands of LL37 and may also inhibit and/or interfere with LL37 function, such as by binding to LL37.

3 Claims, 5 Drawing Sheets

NUCLEIC ACID LIGANDS TO LL37

CROSS-REFERENCE TO RELATED APPLICATIONS

This application claims the benefit of U.S. provisional patent application Ser. No. 61/412,929, filed Nov. 12, 2010, entitled "NUCLEIC ACID LIGANDS TO LL37", the entire contents of which are hereby incorporated by reference.

SEQUENCE LISTING

The nucleotide sequences:

SEQ1   5'-GATCCTATGCTTGACTTAGTTAAAGTCGATCGTCATTCAGA-3'

SEQ2   5'-GCAAAAAGAGACAAGCAACGACCAGTTGACGTTAAGTATA-3'

SEQ3   5'-AATGCTTATTCAATTAATAGAGCCCGCAAGGCCAACACTAATAACACTGAAACCT-3'

SEQ4   5'-GGAATAACAGTGAGTTCTTAAGCCATAGGTCTTAATAACA-3'

SEQ5   5'-GATGTTAACGAACTTCGCCAAAGCACCACGCACATCCGAG-3'

SEQ6   5'-ATTCATTCGAGTCATTATTGCAAAGGCGCGCAAGCAAATC-3'

SEQ7   5'-ACTGGGTCTCACCATCGAAAATCGAAATGACTAAAAGGCC-3'

SEQ8   5'-ATTTCTCTGGACTTGGGTATCGATTATAATCTATCAAAAC-3'

SEQ9   5'-CGAATAGAGGAATATGAGTGCTTGTATCTAACTGTGAATC-3'

SEQ10  5'-CNGGATGAACAGAAAGAAGAGTTTGACTAATACATACTAC-3'

SEQ11  5'-TTATGGCAAGCGAGATGAACAAAAAATATTGTATCAAACC-3'

SEQ12  5'-GATTACTTTTTAACTCTGAAGAGGGTTTCTTTTTGACAAG-3'

SEQ13  5'-ATGACAAAATATATGGTCCCTATTATAAAGTAAAATGTAG-3'

SEQ14  5'-TGAAAAGCGAAATTCTCGTTGTACAGCTATATTTAGAACGGTCTACATAATACAC-3'

SEQ15  5'-GGGTGTATTTCAGAAGTTCGATGAATAATACACACTTCAC-3'

SEQ16  5'-TGTTTGTAGGATTTTTTAGAGACATACTTTACTTTCTCT-3'

SEQ17  5'-TCATATTAAAACCACCGTTGAGATTATAGAACACCAACTG-3'

SEQ18  5'-CCATACGGACGAGAGTATATGTGGGATTGTCCACACAGTC-3'

SEQ19  5'-CTAAAATTAATCTTTCATGGTATGATTGTTTAACCACCAC-3'

SEQ20  5'-GTACGACCTAGACCGTCATAGGGATTTACATCGTAAAAAT-3'

SEQ21  5'-ACAGACGATCATGGCTTGAATTAAAGGAGATAAGTAAAGC-3'

SEQ22  5'-GGGGCTTACAAAAATCTTATGTTTTCTATAAAAGGACTA-3'

SEQ23  5'-ATGTAAAATAATACAATACGGAAACTTCCCATATCACATCAGATAGTAAGTGCAATCT-3'

SEQ24  5'-GCGCATTCTAAAATCGAGGAAAAGAAAAATCGCATCCTTGAGATAGTAAGTGCAA-3'

SEQ25  5'-AGGGGGGAAACCCCTTGGGATGGCATGATTCTCTACTAGAAGATAGTAAGTGCAA-3'

SEQ26  5'-TGAATGGTACTGAAGCTTCTGGATATTTCACTTTAGACAT-3'

SEQ27  5'-CTATGATAAACAATGGTCTTTGCTTTTTAATAAACTAGAC-3'

SEQ28  5'-CGATATTTGGATATGTCCATCTTGATTTGCTTATGACATC-3'

SEQ29  5'-GCAGATTAAATCGGTTTTTTACGACGACTAGTAGAGTATC-3'

SEQ30  5'-TGACAGATAATAACGGCGGTGGAAAGCTATACATCCGAGT-3'

SEQ31  5'-AGGGATCAATTAAAGTAAAGCTAGGAGTATATTAAATGTG-3'

SEQ32  5'-TCACCTATCAAAAGACAATAATTCACTTCAAGTCAACTAT-3'

SEQ33  5'-TTATTATTGAGTTTCAGCCATCTATAAATTAACAAAACGT-3'

SEQ34  5'-AGGAATGAAACTACACCCGGCCTCAAATCCGAGATCCATC-3'

SEQ35  5'-GCCGTTGATGTATTGCTTTGAAGTGANNNGAGGCGAAATCGCGCAAACCATACCCAAAAC-3'

SEQ36  5'-CGACAACNAGAACGAATGCTACCTATTCTACCATCCAATA-3'

SEQ37  5'-CATTATTTAAACAAGAATTTCGAACACAACAAGGCCACGA-3'

SEQ38  5'-AATGATTTTATANNNNACATGTTATCACCCAGCTGTATCC-3'

SEQ39  5'-ATGAAATGTATTATTATAGCAGGTGATAAAAACCAAGTTA-3'

SEQ40  5'-GAAGTATTCAAATGTAAAAAGTGTAGCATAATCACACTGA-3'

SEQ41  5'-CGCGAGAACTTTACCCTTATCTCGACGACTTTCTTATCT-3'

SEQ42  5'-GTTTAAAAGCCTCGCGGATTTCAGTAAACCATTCTTTCTC-3'

SEQ43  5'-TAGTATAAAAGGGTATAAAAAAAATTCACAATCTCGTTTG-3', are hereby incorporated by reference to the ASCII text file entitled "P1014US00_ST25.txt", created Nov. 9, 2010, of 9,029 bytes in size.

FIELD OF THE INVENTION

This invention relates to nucleic acid ligands to LL37, methods for producing said nucleic acid ligands, and methods for utilizing said nucleic acid ligands.

BACKGROUND OF THE INVENTION

Psoriasis and rosacea are chronic inflammatory autoimmune skin disorders which affect a significant portion of people in the U.S. Although these disorders are not life-threatening, they can lead to a significantly poor quality of life and negatively impact the mental health of the patients, leading in severe cases to depression and even suicidal tendencies. There are five approved biological therapeutics on the market for psoriasis (none for rosacea), and all of these are systemic immune suppressors.

The hallmarks of psoriasis are the chronic formation of itchy and scaly plaques, excessive skin inflammation, and hyperkeratinization. The most common form is plaque psoriasis (psoriasis vulgaris), but there are numerous different clinical manifestations of psoriasis, including a form involving joint inflammation and another which affects the nails. The exact causes of psoriasis are unknown, but genetic predisposition and environmental stressors are implicated. Psoriasis affects 2-3% of the worldwide population, and 4.5 million people in the U.S. suffer from the disease. The current modes of treatment include topical corticosteroids or systemic biologics.

Rosacea is another autoimmune disease predominantly affecting the skin, which affects 14 million in the U.S. alone. The manifestations of rosacea include persistent reddening of the skin, mainly in the face, possibly accompanied by stinging, itching sensations, and/or swelling. The onset of rosacea is usually triggered by a wide variety of environmental stressors, including diet, exercise, or weather changes. LL37 may also play a significant role in systemic lupus erythematosus (SLE or "lupus"). Thus, targeting the peptide with a nucleic acid or nucleic acid-like inhibitor may prove to be a highly effective treatment.

Recent research has highlighted the overexpression of a 37-amino acid human antimicrobial peptide named LL37 in the pathogenesis of psoriasis, and independently implicated LL37 in rosacea.

SUMMARY OF THE INVENTION

The present invention is directed to nucleic acid ligands to LL37, methods for producing said nucleic acid ligands, and methods for utilizing said nucleic acid ligands. In one exemplary embodiment, for example, this invention relates to nucleic acid ligands exhibiting high specific binding affinity to LL37 peptides, precursors and/or portions thereof. Further, the nucleic acid ligands may bind competitively with native ligands of LL37 and may also inhibit and/or interfere with LL37 function, such as by binding to LL37.

In one aspect of the present invention, nucleic acid ligands may be or may include aptamers that are, or including but not limited to, single-stranded nucleic acid, such as, for example, single-stranded DNA (ssDNA), single-stranded RNA (ssRNA), and/or a combination thereof; at least a portion of double-stranded nucleic acid, such as, for example, double-stranded DNA (dsDNA), double-stranded RNA (dsRNA), and/or combinations thereof; modified nucleotides and/or other useful molecules, moieties, and/or other functional chemical components, or combinations thereof; or combinations thereof or similar.

In general, the nucleic acid ligands may bind with relatively high specificity to a given target and may further act in a functional manner, such as with agonist or antagonist activity. Further, the nucleic acid ligands may also bind at least partially in competition with a native biomolecule.

In an exemplary embodiment, the nucleic acid ligands may bind to and inhibit at least a portion of the function of LL37 peptides, such as, for example, by inhibiting the functional binding of LL37 to a native ligand, such as, for example, self DNA. In some embodiments, the nucleic acid ligands may be applied to a tissue of a patient such that the nucleic acid ligands may bind to and/or inhibit the function of LL37 in the tissue. In some exemplary embodiments, the nucleic acid ligands may also be modified, enhanced and/or substituted such that they may have increased transport efficiency across, for example, a tissue boundary, such as the skin of a patient. For example, nucleic acid ligands may incorporate modified nucleobases which may, for example, aid in increasing permeability of the nucleic acid ligands through a tissue boundary. The nucleic acid ligands may also be applied to the tissue of a patient using active and/or forced transport methods.

Nucleic acid ligands may be generated and/or selected as aptamers utilizing selective propagation methods. In some exemplary embodiments, nucleic acid ligands may be generated as aptamers from large random libraries, for example, of nucleic acids, utilizing an iterative process, such as the process called Systematic Evolution of Ligands by Exponential Enrichment (SELEX), and/or modifications or similar techniques to SELEX. Resultant aptamers may be further screened for a particular functional activity, such as, for example, antagonist activity against LL37. Appropriate aptamers may then be produced on a large scale at a relatively low cost utilizing nucleic acid synthesis and/or other nucleic acid production methods, which may include cloning and/or fermentation methods. The binding affinity of the aptamers may also be determined, for example, by surface plasmon resonance (SPR) techniques. The permeability through tissue may also be determined, for example, by fluorescence permeability studies.

The present invention together with the above and other advantages may best be understood from the following detailed description of the exemplary embodiments and of the invention illustrated in the drawings.

DETAILED DESCRIPTION OF THE INVENTION

The detailed description set forth below is intended as a description of the presently exemplified embodiments provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices, compositions and materials similar or equivalent to those described herein can be used in the practice or testing of the invention, the exemplified methods, devices, compositions and materials are now described.

All publications mentioned herein are incorporated herein by reference for the purpose of describing and disclosing, for example, the compositions and methodologies that are described in the publications which might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

The present invention is directed to nucleic acid ligands to LL37, methods for producing said nucleic acid ligands, and methods for utilizing said nucleic acid ligands. In one exemplary embodiment, for example, this invention relates to nucleic acid ligands exhibiting high specific binding affinity to LL37 peptides, precursors and/or portions thereof. Further, the nucleic acid ligands may bind competitively with native ligands of LL37 and may also inhibit and/or interfere with LL37 function, such as by binding to LL37.

In one aspect of the present invention, nucleic acid ligands may be or may include aptamers. An "aptamer" refers to a biomolecule that is capable of binding to a particular molecule of interest with high affinity and specificity. The binding of a target to an aptamer, which may be a nucleic acid such as RNA or DNA, or a combination thereof, or a peptide sequence, may generally derive from secondary and/or three-dimensional (3D) structures of the aptamer and the binding may also change the conformation and/or structure of the aptamer. This type of interaction, with a small molecule metabolite, for example, coupled with subsequent changes in aptamer function where the aptamer may be an RNA, may be referred to as a 'riboswitch'. Aptamers may also include non-natural nucleotides, nucleotide analogs, non-natural amino acids and/or amino acid analogs. The method of selection may be by, but is not limited to, affinity chromatography and the method of amplification by reverse transcription (RT), polymerase chain reaction (PCR) and/or any other appropriate amplification method. Aptamers may include specific binding regions which may be capable of binding, attaching, and/or forming complexes with an intended target in an environment wherein other substances in the same environment may not bound, attached, and/or complexed to the aptamer. The specificity of the binding may be defined in terms of the comparative dissociation constants (Kd) of the aptamer for its target as compared to the dissociation constant of the aptamer for other materials in the environment or unrelated molecules in general. Typically, the Kd for the aptamer with respect to its target may be at least about 10-fold less than the Kd for the aptamer with unrelated material and/or accompanying material in the environment. In another example, the Kd may be at least about 50-fold less, in a further example, at least about 100-fold less, and in some exemplary examples at least about 200-fold less. A nucleic acid aptamer may typically be between about 10 and about 300 nucleotides in length, for example. In general, an aptamer may also be between about 30 and about 100 nucleotides in length. The terms "nucleic acid molecule" and "polynucleotide" may refer to deoxyribonucleotides or ribonucleotides and polymers thereof in either single- or double-stranded form. In general, the term may refer to nucleic acids containing known analogues of natural nucleotides which may have similar binding properties as the reference nucleic acid and may be metabolized in a manner similar to naturally occurring nucleotides. A particular nucleic acid sequence may also implicitly encompass conservatively modified variants thereof (e.g., degenerate codon substitutions) and/or complementary sequences, as well as the sequence. Degenerate codon substitutions may be achieved by generating sequences in which the third position of one or more selected (or all) codons may be substituted with mixed-base and/or deoxyinosine residues. Also included may be molecules that may have naturally occurring phosphodiester linkages as well as those that may have non-naturally occurring linkages, e.g., for stabilization purposes. The nucleic acid may be in any physical form, such as e.g., linear, circular, or supercoiled. The term nucleic acid may also be used interchangeably with oligonucleotide, gene, cDNA, and mRNA encoded by a gene.

Aptamers may further include, but are not limited to, single-stranded nucleic acid, such as, for example, single-stranded DNA (ssDNA), single-stranded RNA (ssRNA), and/or a combination thereof; at least a portion of double-stranded nucleic acid, such as, for example, double-stranded DNA (dsDNA), double-stranded RNA (dsRNA), and/or combinations thereof; modified nucleotides and/or other useful molecules, moieties, and/or other functional chemical components, or combinations thereof; or combinations thereof or similar.

In general, modified nucleic acid bases may be utilized and may include, but are not limited to, 5-Propynyl-2'-deoxycytidine-5'-Triphosphate, C8-alkyne-dCTP, 2'-Deoxy-P-nucleoside-5'-Triphosphate, 2'-Deoxyinosine-5'-Triphosphate, 2'-Deoxypseudouridine-5'-Triphosphate, 2'-Deoxyuridine-5'-Triphosphate, 2'-Deoxyzebularine-5'-Triphosphate, 2-Amino-2'-deoxyadenosine-5'-Triphosphate, 2-Amino-6-chloropurine-2'-deoxyriboside-5'-Triphosphate, 2-Aminopurine-2'-deoxyribose-5'-Triphosphate, 2-Thio-2'-deoxycytidine-5'-Triphosphate, 2-Thiothymidine-5'-Triphosphate, 2'-Deoxy-L-adenosine-5'-Triphosphate, 2'-Deoxy-L-cytidine-5'-Triphosphate, 2'-Deoxy-L-guanosine-5'-Triphosphate, 2'-Deoxy-L-thymidine-5'-Triphosphate, 4-Thiothymidine-5'-Triphosphate, 5-Aminoallyl-2'-deoxycytidine-5'-Triphosphate, 5-Aminoallyl-2'-deoxyuridine-5'-Triphosphate, 5-Bromo-2'-deoxycytidine-5'-Triphosphate, 5-Bromo-2'-deoxyuridine-5'-Triphosphate, 5-Fluoro-2'-deoxyuridine-5'-Triphosphate, and/or any other appropriate modified nucleic acid base. It may generally be understood that the nucleoside triphosphates (NTPs) listed above may generally refer to any appropriate phosphate of the modified base, such as additionally, for example, monophosphates (NMPs) or diphosphates (NDPs) of the base. Examples of modified pyrimidine nucleosides are disclosed in U.S. Pat. No. 6,369,040, the entire contents of which are hereby incorporated by reference.

In general, the nucleic acid ligands may bind with relatively high specificity to a given target and may further act in a functional manner, such as with agonist or antagonist activity. Further, the nucleic acid ligands may also bind at least partially in competition with a native biomolecule.

Nucleic acid ligands may be generated and/or selected as aptamers utilizing selective propagation methods. In some exemplary embodiments, nucleic acid ligands may be generated as aptamers from large random libraries, for example, of nucleic acids, utilizing an iterative process, such as the process called Systematic Evolution of Ligands by Exponential Enrichment (SELEX), and/or modifications or similar techniques to SELEX. Resultant aptamers may be further screened for a particular functional activity, such as, for example, antagonist activity against LL37. Appropriate aptamers may then be produced on a large scale at a relatively low cost utilizing nucleic acid synthesis and/or other nucleic acid production methods, which may include cloning and/or fermentation methods. The binding affinity of the aptamers may also be determined, for example, by surface plasmon resonance (SPR) techniques. The permeability through tissue may also be determined, for example, by fluorescence permeability studies.

In general, generated aptamers may also be analyzed, such as by sequencing, sequence clustering, folding, conformation and/or shape determination, motif-identification, and/or by any other appropriate method of analysis or combination thereof. For example, after multiple rounds of selection in SELEX, particular sequence motifs and/or clusters may emerge as dominant. This may be useful, for example, in determining particular aptamer features that may play a substantial role in the binding activity of the aptamers.

Figure 1:
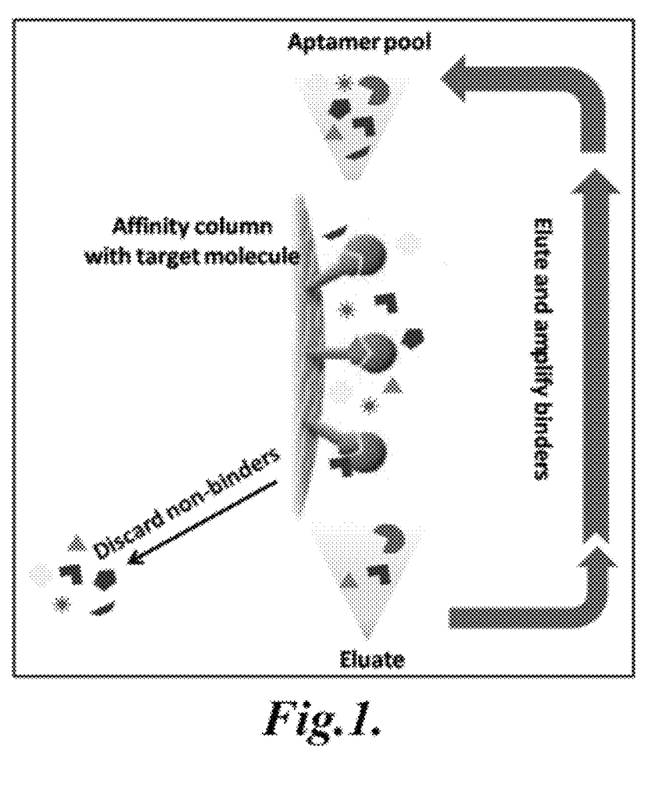
FIG. 1 illustrates an example of SELEX.

In general, as illustrated in FIG. 1, the SELEX method may include contacting a library of, for example, nucleic acids with at least one target, such as, for example, whole cell(s); target molecules, such as isolated and/or partially isolated receptor molecules; and/or any other appropriate target. In general, the members of the library that do not bind with some affinity to the target may be washed or otherwise partitioned from the remainder of the library, which may have a given level of binding affinity to the target. Washing and/or partitioning may in general include any appropriate method and/or mechanism of separating non-binding molecules, such as, for example, agitation, aspiration, flushing, and/or any other appropriate method, mechanism, or combination thereof. Flushing and/or otherwise employing a fluid for washing may generally utilize the same or similar fluid as the fluid utilized as the binding environment. The process may be repeated to partition the strongest binding members of the library. Binding may generally refer to forming a molecular complex, chemical bond, physical attachment and/or any other general intermolecular association, interaction and/or attachment. Also in general, the separating force of the washing and/or partitioning method or mechanism may generally set at least a partial threshold of binding affinity for an nucleic acids that may remain after the washing and/or partitioning step. Amplification, such as by PCR and/or other appropriate nucleic acid amplification methods, of the binding library members may also be utilized to increase the numbers of the binding members of the library for subsequent repetitions and for isolation and/or purification of any final products of the process. Embodiments of the SELEX method may generally be utilized to achieve the generation of functional biomolecules of a given binding affinity and/or range of binding affinity. The various steps of SELEX and related protocols or modifications thereof may be performed in general, utilizing appropriate conditions, such as, for example, an appropriate buffer and/or binding environment, which may be, for example, the same or similar to an environment where generated aptamers may be utilized. For cell receptor molecules and/or other molecules that bind particular molecules as their function, an appropriate physiological buffer and/or environment may generally be utilized for SELEX protocols. Collection of product aptamers may be achieved by, for example, elution of the nucleic acids utilizing an unfavorable environment or buffer for binding to the target, such as, for example, high osmolarity solution, which may in general interfere with binding ability of the nucleic acids. Any other appropriate collection method may also be utilized. Details of a basic SELEX protocol may be found in U.S. Pat. No. 5,270,163, entitled "Methods for identifying nucleic acid ligands," the entire contents of which are hereby incorporated by reference. Other SELEX protocols that may generally be utilized and/or modified for an appropriate usage include those found in U.S. Pat. No. 5,789,157, entitled "Systematic evolution of ligands by exponential enrichment: tissue selex," the entire contents of which are hereby incorporated by reference.

The SELEX technique may begin with a large library of random nucleotides or aptamers. The library may then be contacted with a target and the aptamers bound to the target may be separated and amplified for the next round. The binding conditions for each round may be made more stringent than in the previous round until the only remaining aptamers in the pool are highly specific for and bind with high affinity to the target. While aptamers may be analogous to antibodies in their range of target recognition and variety of applications, they may also possess several key advantages over their protein counterparts. For example, they are generally smaller, easier and/or more economical to produce, are capable of greater specificity and affinity, are highly biocompatible and non-immunogenic, and/or can easily be modified chemically to yield improved properties, for example, any desired properties. After selection, the selected aptamers may also be produced by chemical synthesis, which may aid in eliminating batch-to-batch variation which complicates production of therapeutic proteins.

In some exemplary embodiments, SELEX may be performed to generate aptamers utilizing a whole-cell and/or tissue approach. This may be desirable as whole-cell and/or tissue targets may present appropriate target molecules in a "native" state, such as living target cells with active and/or operative target molecules. In some embodiments, non-whole-cell targets may also be utilized, which may include, but are not limited to, purified molecular samples, anchored target molecules, artificial micelles and/or liposomes presenting target molecules, and/or any other appropriate target.

In an exemplary embodiment, the nucleic acid ligands may bind to and inhibit at least a portion of the function of LL37 peptides, such as, for example, by inhibiting the functional binding of LL37 to a native ligand, such as, for example, self DNA. Examples of nucleic acid ligands that have been generated that may bind to LL37 are incorporated herein by reference to the sequence IDs SEQ1-SEQ43.

Figure 2:
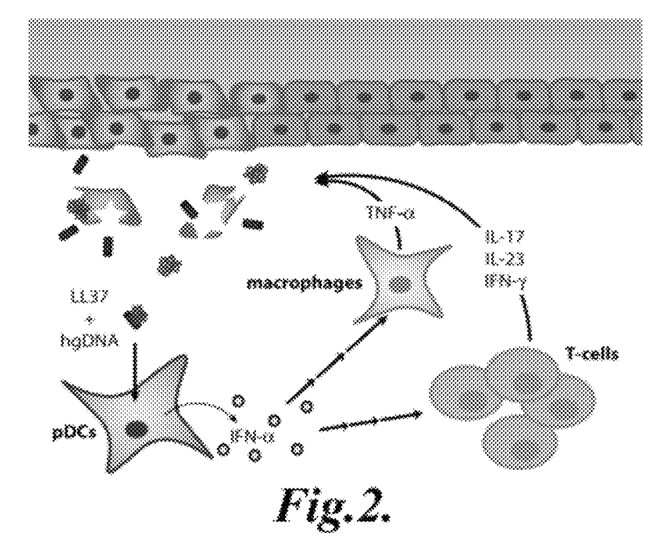
FIG. 2 illustrates a mechanism for psoriasis.

For example, and without wishing to be bound by any particular theory, cationic antimicrobial peptides have been shown to be an integral part of innate immune responses, and are found in many classes of organisms. These small peptides (~10-50 residues) are produced by the host organism and may interact with the negatively-charged membranes of pathogens such as bacteria and fungi. In higher organisms, these peptides have been also found to interact with and modulate host immune systems. One family of the cationic antimicrobial peptides are the cathelicidin peptides, which are common in mammals, but only one cathelicidin has been identified in humans. This peptide is expressed as a precursor (CAP-18) which is subsequently proteolytically processed to produce a 37-amino acid cationic peptide of 4.5 kDa, called LL37. LL37 has also been shown to be processed differentially in a tissue-dependent manner, to produce various peptides with varying antimicrobial activities. Previous research has demonstrated that LL37 has potent antimicrobial activity, can attenuate host responses to lipopolysaccharides (LPS), influences cytokine secretion of various tissues, and can directly activate different immune cells to produce a wide variety of responses. Thus, in over 300 published studies this small peptide has been shown to play a pivotal role in the interplay of inflammation, pathogen response, and immune modulation. The antimicrobial effects of LL37 have led to its development as an antimicrobial agent for dental caries, antibiotic-resistant pathogens, and even for coating prosthetic devices. In addition, it has been investigated as a potential cancer therapeutic due to its anti-tumor activities in specific cancers. However, LL37 is also implicated in the onset of some diseases. In particular types of cancers, LL37 expression actually increases proliferation. There has also been a study linking the expression of LL37 to the pathogenesis of atherosclerosis. By far, the most established finding of LL37 dysfunction leading to a specific disorder has been the well-investigated link of LL37 overexpression leading to the emergence and/or propagation of psoriasis. LL37 promotes an autoimmune response by binding to self-DNA extracellularly and activating plasmacytoid dendritic cells (pDC) to produce IFN-α. The LL37-DNA binding was demonstrated to be non-specific, as DNA isolated from non-psoriasis patients also induced expression of IFN-α. As shown in FIG. 2, LL37 binds to extracellular self-DNA allowing its internalization into endocytic compartments of plasmacytoid dendritic cells (pDCs) where it triggers Toll-like receptor (TLR)-9 activation. Research has demonstrated that LL37 is constantly overexpressed in psoriatic skin leading to the formation of LL37-DNA complexes that induce chronic activation of pDC with production of high levels of IFN-α. The overexpression of IFN-α initiates the local activation of autoimmune T-cells and may lead to the development of psoriatic lesions.

Figure 3:
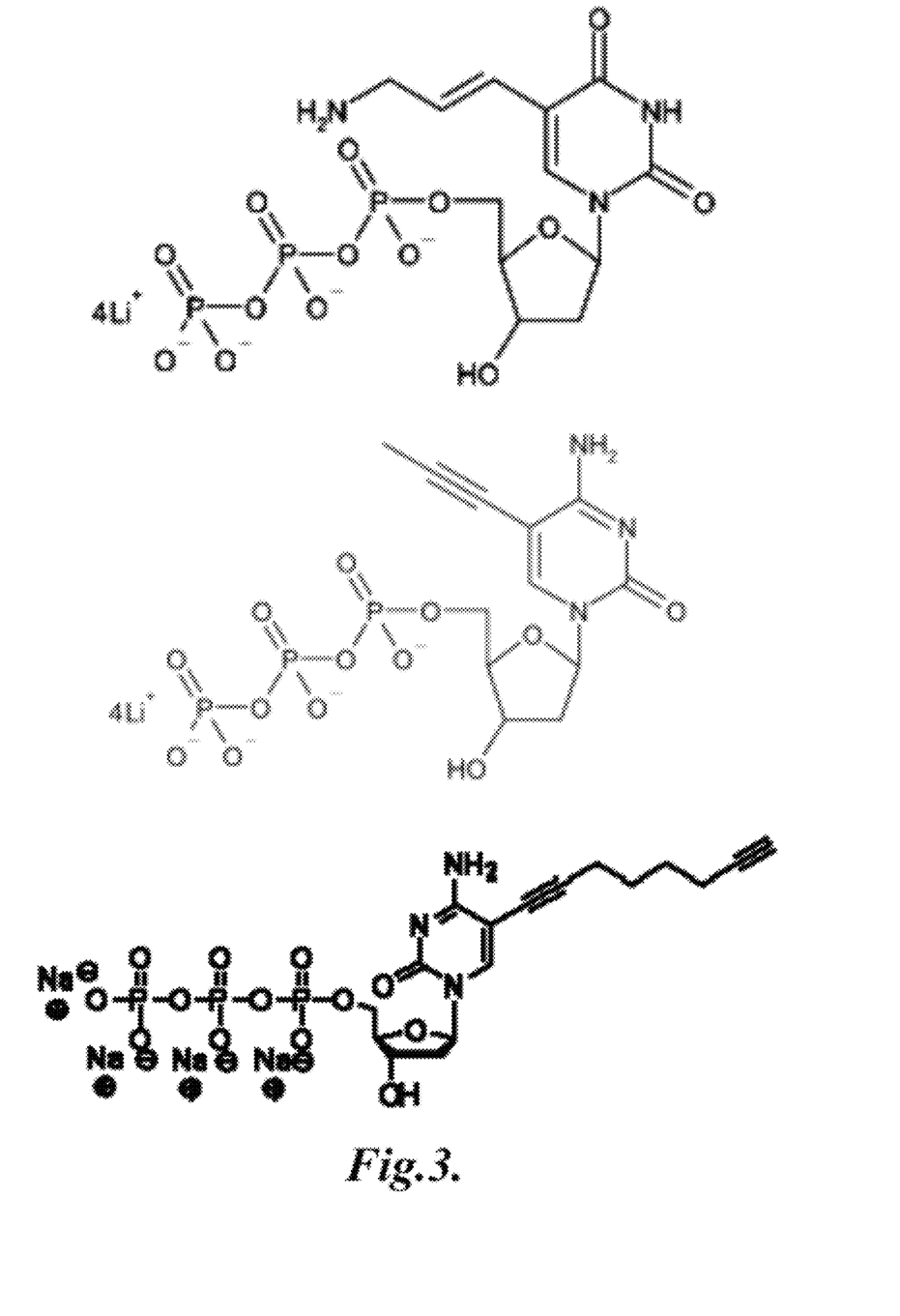
FIG. 3 shows examples of modified nucleobases.

In some embodiments, the nucleic acid ligands may be applied to a tissue of a patient such that the nucleic acid ligands may bind to and/or inhibit the function of LL37 in the tissue. In some exemplary embodiments, the nucleic acid ligands may also be modified, enhanced and/or substituted such that they may have increased transport efficiency across, for example, a tissue boundary, such as the skin of a patient. For example, nucleic acid ligands may incorporate and/or include modified nucleobases which may, for example, aid in increasing permeability of the nucleic acid ligands through a tissue boundary. For example, during amplification or synthesis, modified nucleobases such as alkene- or alkyne-modified bases which may include, but are not limited to, Aminoallyl deoxyUTP, 5-Propynyl-2'-deoxycytidine-5'-Triphosphate, C8-alkyne-dCTP, as shown in FIG. 3, and/or any other appropriate modified base. Without wishing to be bound by any particular theory, higher bond-order modified bases may generally have increased permeability through tissue, such as lipid-rich and proteinaceous tissues which may include skin. The nucleic acid ligands may also be applied to the tissue of a patient using active and/or forced transport methods, such as, for example, electrophoresis, sonophoresis, and/or any other appropriate method or combination thereof. The nucleic acid ligands may also be dissolved in a solvent, such as, for example DMSO, which may improve and/or enhance permeability.

In some embodiments, multimeric or chimeric aptamers may be generated which may include multiple binding sites for at least one target. For example, a chimeric aptamer may be generated from two or more aptamers joined by a linking sequence which may include, for example, an oligonucleotide sequence or other polymeric linkage. In some embodiments, multimeric aptamers may be generated utilizing, for example, rolling circle amplification, such as from a circular DNA template, and/or any other appropriate method. A chimeric aptamer may, for example, be utilized to bind multiple sites of a target, such as LL37.

The following examples were carried out as exemplary illustrations of the present invention and are not to be construed to be limiting in any manner.

EXAMPLES

1. Verification of Aptamer Binding with Surface Plasmon Resonance (SPR)

Figure 4:
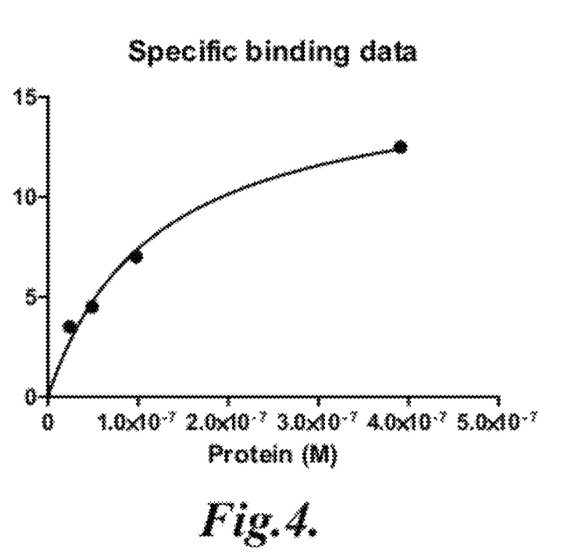
FIG. 4 shows an example of a binding curve for an aptamer to LL37 measured by surface plasmon resonance (SPR)

Aptamers were immobilized to the test channel of a neutravidin-coated SPR chip via standard biotin modification. A nonsense DNA was immobilized on the reference channel to identically match the electrostatic conditions of each channel, and then increasing concentrations of target protein LL37 were added such that no regeneration steps are required. The differential response to each dose was extracted and fit to a binding isotherm model to accurately determine Kd. Binding curves for sequence ID SEQ7 is shown in FIG. 4, yielding a Kd of 117.9 nM.

2. Inhibition of IFN-α Production in pDC Cell Culture with LL37 and Aptamers

Figure 5:
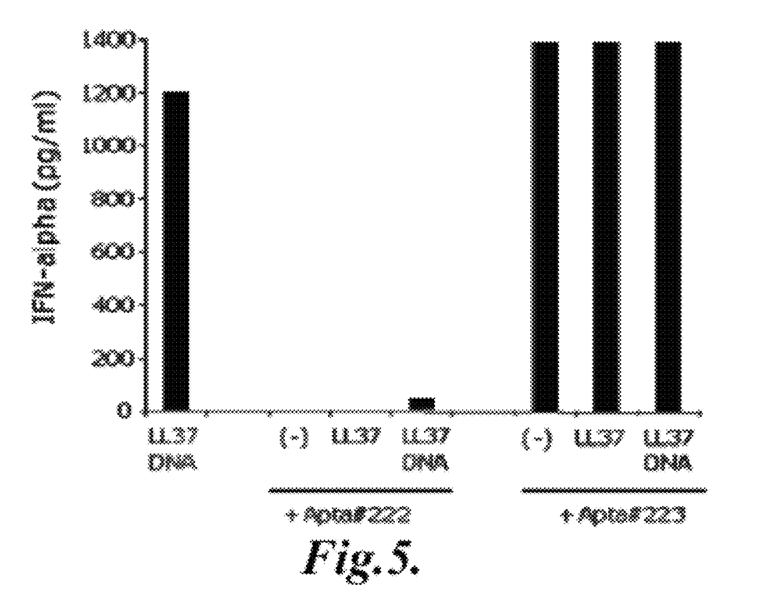
FIG. 5 shows an example of the effect of an LL37 aptamer on the production of LL37 in cell culture.

Preliminary investigations were performed to determine the feasibility of using LL37-specific aptamers for competing with human (self) genomic DNA (gDNA) to inhibit pDC activation as a key pathogenic event that leads to psoriasis. Based on the richest folding as determined by mfold, 2 aptamers, sequence IDs SEQ7 and SEQ16, were chosen as additives to pDC cell cultures. pDC cell cultures were incubated with various combinations of LL37, LL37+gDNA, or LL37+gDNA+Aptamer. The LL37 concentration was 10 μM while the aptamer concentration employed was half that at 5 μM. Cell culture supernatants were then assayed by sensitive ELISA for IFN-α. As shown in FIG. 5, SEQ7 (shown as Apta#222) greatly decreased IFN-α production.

3. Example of Enhanced Transport of Modified-Base Aptamers Across Murine Skin

Figure 6:
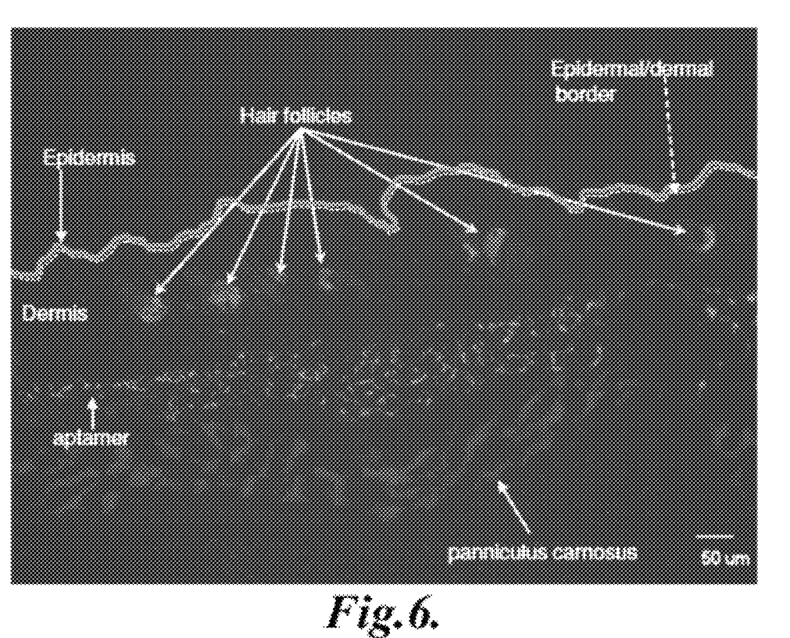
FIG. 6 shows an example of transport of a modified nucleic acid across murine skin.

During PCR amplification of 76-mer DNA, a modified nucleobase was substituted for the natural counterpart. The forward PCR primer was biotinylated, and the reverse primer was phosphorylated to allow specific digestion of the complementary strand using lambda exonuclease such that a single-stranded DNA was created. The purified DNA product was then added to humidified, explanted mouse skin at room temperature at a concentration of 1 μM overnight. Skin samples were then sectioned by cryotome and labeled with a streptavidin fluorophore for fluorescence microscopy. FIG. 6 shows the result for a 76-mer DNA incorporating 5-Propynyl-2'-deoxycytidine-5'-Triphosphate. The applied DNA was dissolved in 2% DMSO to enhance permeability. As shown in FIG. 6, the compound penetrates well into the dermis.

Although various exemplary embodiments have been shown and described, it will be appreciated by those of ordinary skill in the art that the present invention can be embodied in other forms, combinations and modifications without departing from the spirit or essential character hereof. The present description is therefore considered in all respects to be illustrative and not restrictive. The scope of the present invention is intended to be limited only by the appended claims, and all changes that come within the meaning and range of equivalents thereof are intended to be embraced therein.

The invention claimed is:

1. A composition comprising: at least one modified nucleic acid ligand having a nucleic acid sequence of SEQ ID NO: 7.

2. The composition of claim 1, wherein said at least one modified nucleic acid ligand comprises at least one alkyne-modified nucleobase.

3. The composition of claim 2, wherein said alkyne-modified nucleobase is selected from the group consisting of Amino-allyl deoxyUTP, 5-Propynyl-2'-deoxycytidine-5'-Triphosphate, and C8-alkyne-dCTP.

* * * * *

SEQUENCE LISTING

<160> NUMBER OF SEQ ID NOS: 43

<210> SEQ ID NO 1
<211> LENGTH: 41
<212> TYPE: DNA
<213> ORGANISM: Artificial Sequence
<220> FEATURE:
<223> OTHER INFORMATION: DNA Aptamer for Human LL37

<400> SEQUENCE: 1
gatcctatgc ttgacttagt taaagtcgat cgtcattcag a                41

<210> SEQ ID NO 2
<211> LENGTH: 40
<212> TYPE: DNA
<213> ORGANISM: Artificial Sequence
<220> FEATURE:
<223> OTHER INFORMATION: DNA Aptamer for Human LL37

<400> SEQUENCE: 2
gcaaaaagag acaagcaacg accagttgac gttaagtata                  40

<210> SEQ ID NO 3
<211> LENGTH: 55
<212> TYPE: DNA
<213> ORGANISM: Artificial Sequence
<220> FEATURE:
<223> OTHER INFORMATION: DNA APTAMER FOR HUMAN LL37

<400> SEQUENCE: 3
aatgcttatt caattaatag agcccgcaag gccaacacta ataacactga aacct     55

<210> SEQ ID NO 4
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 4
ggaataacag tgagttctta agccataggt cttaataaca                  40

<210> SEQ ID NO 5
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 5
gatgttaacg aacttcgcca aagcaccacg cacatccgag                  40

<210> SEQ ID NO 6
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 6
attcattcga gtcattattg caaaggcgcg caagcaaatc                  40

<210> SEQ ID NO 7
<211> LENGTH: 40
<212> TYPE: DNA
<213> ORGANISM: Artificial Sequence

```
<220> FEATURE:
<223> OTHER INFORMATION: DNA APTAMER FOR HUMAN LL37

<400> SEQUENCE: 7
actgggtctc accatcgaaa atcgaaatga ctaaaaggcc                                40

<210> SEQ ID NO 8
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 8
atttctctgg acttgggtat cgattataat ctatcaaaac                                40

<210> SEQ ID NO 9
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 9
cgaatagagg aatatgagtg cttgtatcta actgtgaatc                                40

<210> SEQ ID NO 10
<211> LENGTH: 40
<212> TYPE: DNA
<213> ORGANISM: Artificial Sequence
<220> FEATURE:
<223> OTHER INFORMATION: DNA APTAMER FOR HUMAN LL37
<220> FEATURE:
<221> NAME/KEY: misc_feature
<222> LOCATION: (2)..(2)
<223> OTHER INFORMATION: n is a, c, g, or t

<400> SEQUENCE: 10
cnggatgaac agaaagaaga gtttgactaa tacatactac                                40

<210> SEQ ID NO 11
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 11
ttatggcaag cgagatgaac aaaaaatatt gtatcaaacc                                40

<210> SEQ ID NO 12
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 12
gattactttt taactctgaa gagggtttct ttttgacaag                                40

<210> SEQ ID NO 13
<211> LENGTH: 40
<212> TYPE: DNA
<213> ORGANISM: Artificial Sequence
<220> FEATURE:
<223> OTHER INFORMATION: DNA APTAMER FOR HUMAN LL37
```

<400> SEQUENCE: 13
atgacaaaat atatggtccc tattataaag taaaatgtag                                  40

<210> SEQ ID NO 14
<211> LENGTH: 55
<212> TYPE: DNA
<213> ORGANISM: Artificial Sequence
<220> FEATURE:
<223> OTHER INFORMATION: DNA APTAMER FOR HUMAN LL37

<400> SEQUENCE: 14
tgaaaagcga aattctcgtt gtacagctat atttagaacg gtctacataa tacac              55

<210> SEQ ID NO 15
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 15
gggtgtattt cagaagttcg atgaataata cacacttcac                                  40

<210> SEQ ID NO 16
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 16
tgtttgtagg atttttttag agacatactt tactttctct                                  40

<210> SEQ ID NO 17
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 17
tcatattaaa accaccgttg agattataga acaccaactg                                  40

<210> SEQ ID NO 18
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 18
ccatacggac gagagtatat gtgggattgt ccacacagtc                                  40

<210> SEQ ID NO 19
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 19
ctaaaattaa tctttcatgg tatgattgtt taaccaccac                                  40

<210> SEQ ID NO 20
<211> LENGTH: 40

```
<212> TYPE: DNA
<213> ORGANISM: Artificial Sequence
<220> FEATURE:
<223> OTHER INFORMATION: DNA APTAMER FOR HUMAN LL37

<400> SEQUENCE: 20
gtacgaccta gaccgtcata gggatttaca tcgtaaaaat                          40

<210> SEQ ID NO 21
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 21
acagacgatc atggcttgaa ttaaaggaga taagtaaagc                          40

<210> SEQ ID NO 22
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 22
ggggcttaca aaatcttat gtttttctat aaaaggacta                           40

<210> SEQ ID NO 23
<211> LENGTH: 58
<212> TYPE: DNA
<213> ORGANISM: Artificial Sequence
<220> FEATURE:
<223> OTHER INFORMATION: DNA APTAMER FOR HUMAN LL37

<400> SEQUENCE: 23
atgtaaaata atacaatacg gaaacttccc atatcacatc agatagtaag tgcaatct      58

<210> SEQ ID NO 24
<211> LENGTH: 55
<212> TYPE: DNA
<213> ORGANISM: Artificial Sequence
<220> FEATURE:
<223> OTHER INFORMATION: DNA APTAMER FOR HUMAN LL37

<400> SEQUENCE: 24
gcgcattcta aaatcgagga aagaaaaat cgcatccttg agatagtaag tgcaa          55

<210> SEQ ID NO 25
<211> LENGTH: 55
<212> TYPE: DNA
<213> ORGANISM: Artificial Sequence
<220> FEATURE:
<223> OTHER INFORMATION: DNA APTAMER FOR HUMAN LL37

<400> SEQUENCE: 25
aggggggaaa ccccttggga tggcatgatt ctctactaga agatagtaag tgcaa         55

<210> SEQ ID NO 26
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 26
```
tgaatggtac tgaagcttct ggatatttca ctttagacat        40

<210> SEQ ID NO 27
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 27
ctatgataaa caatggtctt tgcttttaa taaactagac        40

<210> SEQ ID NO 28
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 28
cgatatttgg atatgtccat cttgatttgc ttatgacatc        40

<210> SEQ ID NO 29
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 29
gcagattaaa tcggtttttt acgacgacta gtagagtatc        40

<210> SEQ ID NO 30
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 30
tgacagataa taacggcggt ggaaagctat acatccgagt        40

<210> SEQ ID NO 31
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 31
agggatcaat taaagtaaag ctaggagtat attaaatgtg        40

<210> SEQ ID NO 32
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 32
tcacctatca aaagacaata attcacttca agtcaactat        40

<210> SEQ ID NO 33
<211> LENGTH: 40
<212> TYPE: DNA
<213> ORGANISM: Artificial Sequence

```
<220> FEATURE:
<223> OTHER INFORMATION: DNA APTAMER FOR HUMAN LL37

<400> SEQUENCE: 33
ttattattga gtttcagcca tctataaatt aacaaaacgt                           40

<210> SEQ ID NO 34
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 34
aggaatgaaa ctacacccgg cctcaaatcc gagatccatc                           40

<210> SEQ ID NO 35
<211> LENGTH: 60
<212> TYPE: DNA
<213> ORGANISM: Artificial Sequence
<220> FEATURE:
<223> OTHER INFORMATION: DNA APTAMER FOR HUMAN LL37
<220> FEATURE:
<221> NAME/KEY: misc_feature
<222> LOCATION: (27)..(29)
<223> OTHER INFORMATION: n is a, c, g, or t

<400> SEQUENCE: 35
gccgttgatg tattgctttg aagtgannng aggcgaaatc gcgcaaacca tacccaaaac    60

<210> SEQ ID NO 36
<211> LENGTH: 40
<212> TYPE: DNA
<213> ORGANISM: Artificial Sequence
<220> FEATURE:
<223> OTHER INFORMATION: DNA APTAMER FOR HUMAN LL37
<220> FEATURE:
<221> NAME/KEY: misc_feature
<222> LOCATION: (8)..(8)
<223> OTHER INFORMATION: n is a, c, g, or t

<400> SEQUENCE: 36
cgacaacnag aacgaatgct acctattcta ccatccaata                           40

<210> SEQ ID NO 37
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 37
cattatttaa acaagaattt cgaacacaac aaggccacga                           40

<210> SEQ ID NO 38
<211> LENGTH: 40
<212> TYPE: DNA
<213> ORGANISM: Artificial Sequence
<220> FEATURE:
<223> OTHER INFORMATION: DNA APTAMER FOR HUMAN LL37
<220> FEATURE:
<221> NAME/KEY: misc_feature
<222> LOCATION: (13)..(16)
<223> OTHER INFORMATION: n is a, c, g, or t

<400> SEQUENCE: 38 aatgattttta tannnnacat gttatcaccc agctgtatcc                          40
```

```
<210> SEQ ID NO 39
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 39
atgaaatgta ttattatagc aggtgataaa aaccaagtta                              40

<210> SEQ ID NO 40
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 40
gaagtattca aatgtaaaaa gtgtagcata atcacactga                              40

<210> SEQ ID NO 41
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 41
cgcgagaact ttacccttat ctcgacgact ttcttatcat                              40

<210> SEQ ID NO 42
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 42
gtttaaaagc ctcgcggatt tcagtaaacc attctttctc                              40

<210> SEQ ID NO 43
<211> LENGTH: 40
<212> TYPE: DNA
<213> ORGANISM: Artificial Sequence
<220> FEATURE:
<223> OTHER INFORMATION: DNA APTAMER FOR HUMAN LL37

<400> SEQUENCE: 43
tagtataaaa gggtataaaa aaaattcaca atctcgtttg                              40
```